US009827030B2

United States Patent
Vogt et al.

(10) Patent No.: US 9,827,030 B2
(45) Date of Patent: *Nov. 28, 2017

(54) CARTRIDGE SYSTEM HAVING CONNECTED FEED PLUNGERS

(75) Inventors: Sebastian Vogt, Erfurt (DE); Hubert Buechner, Nuremberg (DE)

(73) Assignee: Heraeus Medical GmbH, Wehrheim (DE)

( * ) Notice: Subject to any disclaimer, the term of this patent is extended or adjusted under 35 U.S.C. 154(b) by 1394 days.

This patent is subject to a terminal disclaimer.

(21) Appl. No.: 13/696,214

(22) PCT Filed: Apr. 15, 2011

(86) PCT No.: PCT/EP2011/001919
§ 371 (c)(1),
(2), (4) Date: Apr. 29, 2013

(87) PCT Pub. No.: WO2011/137971
PCT Pub. Date: Nov. 10, 2011

(65) Prior Publication Data
US 2013/0231673 A1    Sep. 5, 2013

(30) Foreign Application Priority Data
May 4, 2010    (DE) .......... 10 2010 019 220

(51) Int. Cl.
*A61B 17/88* (2006.01)
*A61C 5/64* (2017.01)
*B05C 17/005* (2006.01)

(52) U.S. Cl.
CPC ............ *A61B 17/8805* (2013.01); *A61C 5/64* (2017.02); *B05C 17/00513* (2013.01);
(Continued)

(58) Field of Classification Search
CPC ............ B01F 13/0023; B01F 15/0237; B01F 15/0278; B01F 15/0279; B05C 17/00506;
(Continued)

(56) References Cited

U.S. PATENT DOCUMENTS

| 2,125,245 A | 7/1938 | McCray |
| 3,215,298 A | 11/1965 | Shaffer |

(Continued)

FOREIGN PATENT DOCUMENTS

| CH | 669164 A5 | 2/1989 |
| CN | 1835873 A | 9/2006 |

(Continued)

OTHER PUBLICATIONS

Australian Examination Report for corresponding Australian Application No. 2011250315 dated May 8, 2013.

(Continued)

*Primary Examiner* — Anu Ramana
(74) *Attorney, Agent, or Firm* — Norris McLaughlin & Marcus, P.A.

(57) ABSTRACT

Cartridge system for mixing and applying a mix of a medical cement. Cartridges are arranged parallel to each other and an outlet opening. The cartridges each comprise at least one opening that connect(s) the cartridges to the outlet opening, and the cartridges are bordered laterally through cartridge walls. Each cartridge comprises a feed plunger for expelling starting components of the mix from the cartridges through the openings. The feed plungers are fixedly connected to each other through at least one fin. The cartridge walls of the cartridges are connected through the fin(s). The walls comprise slits that are arranged parallel to the cartridge axis, whereby the width of the slits is well-suited for taking up the (Continued)

fin or fins, and the at least one fin moves through regions of the slits when the feed plungers perform a motion in the cartridges.

16 Claims, 5 Drawing Sheets

(52) U.S. Cl.
CPC .. *B05C 17/00553* (2013.01); *B05C 17/00576* (2013.01); *B05C 17/00506* (2013.01)

(58) Field of Classification Search
CPC ........ B05C 17/00513; B05C 17/00553; B05C 17/00576; A61B 17/8811; A61B 17/8819; A61B 17/8822; A61B 17/8825
USPC ......... 366/177.1, 181.4, 181.5, 162.1, 162.3, 366/189; 222/325, 326, 327
See application file for complete search history.

(56) References Cited

U.S. PATENT DOCUMENTS

| | | | |
|---|---|---|---|
| 4,068,830 A | 1/1978 | Gray | |
| 4,260,077 A | 4/1981 | Schroeder | |
| 4,690,306 A | 9/1987 | Staeheli | |
| 5,540,356 A | 7/1996 | Camm et al. | |
| 5,968,018 A | 10/1999 | Freeman et al. | |
| 6,302,574 B1 * | 10/2001 | Chan | A61B 17/8825 222/137 |
| 6,311,871 B1 | 11/2001 | Binder | |
| 6,547,432 B2 * | 4/2003 | Coffeen | A61B 17/8822 366/130 |
| 7,306,361 B2 * | 12/2007 | Coffeen | A61B 17/8822 366/139 |
| 9,095,871 B2 * | 8/2015 | Vogt | B05C 17/00506 |
| 2003/0179648 A1 | 9/2003 | Heusser et al. | |
| 2009/0062808 A1 | 3/2009 | Wolf | |

FOREIGN PATENT DOCUMENTS

| | | |
|---|---|---|
| DE | 2017292 A1 | 10/1971 |
| DE | 2521392 A1 | 11/1976 |
| DE | 3440893 A1 | 5/1986 |
| DE | 102007052116 A1 | 4/2009 |
| DE | 102007050762 B3 | 5/2009 |
| DE | 102008030312 A1 | 1/2010 |
| EP | 0236129 A2 | 9/1987 |
| EP | 0261466 A1 | 3/1988 |
| EP | 0289882 A1 | 11/1988 |
| EP | 0294672 A1 | 12/1988 |
| EP | 0431347 A1 | 6/1991 |
| EP | 0607102 A1 | 7/1994 |
| EP | 0664153 A1 | 7/1995 |
| EP | 0693437 A1 | 1/1996 |
| EP | 0787535 A1 | 8/1997 |
| EP | 1004353 A1 | 5/2000 |
| EP | 2008707 A1 | 12/2008 |
| FR | 2702396 A1 | 9/1994 |
| GB | 1188516 A | 4/1970 |
| GB | 2082686 A | 3/1982 |
| JP | H05139467 A | 6/1993 |
| JP | 2005289470 A | 10/2005 |
| WO | 2006005206 | 1/2006 |
| WO | 2008135714 A1 | 11/2008 |
| WO | 2009036962 A2 | 3/2009 |

OTHER PUBLICATIONS

International Search Report for PCT Application No. PCT/EP2011/001919 dated Oct. 7, 2011.

English-Language Translation Japanese Office Action for corresponding Japanese Application No. 2013-508383 dated Jan. 14, 2014.

Chinese Office Action for corresponding Chinese Application No. 201180022442.0 dated Dec. 26, 2014 along with the English-Language Translation thereof.

* cited by examiner

CARTRIDGE SYSTEM HAVING CONNECTED FEED PLUNGERS

This is an application filed under 35 U.S.C. §371 of PCT/EP2011/001919, filed on Apr. 15, 2011 and claiming priority to DE 10 2010 019 220.1, filed on May 4, 2010.

BACKGROUND OF THE INVENTION

The invention relates to a cartridge system for mixing and applying a mixing ware, in particular a medical cement, comprising at least two cartridges that are arranged parallel to each other, and an outlet opening, whereby the cartridges each comprise at least one opening that connect(s) the cartridges to the outlet opening, and the cartridges are bordered laterally through cartridge walls and each comprise a feed plunger for expelling starting components of the mixing ware from the cartridges through the openings, and whereby at least two feed plungers are fixedly connected to each other.

Cartridge systems for mixing and applying a mixing ware can consist of multiple components and are to ensure safe storage and safe closure for components in at least two cartridges prior to their use. The cartridge system should be safe and easy to open right before the application of the mixing ware, whereby synchronous opening of the individual cartridges is desirable.

Reactive pasty two- or multi-component systems must be stored separately after their production and until their application in order to prevent premature, inadvertent reactions of the components. Cartridge systems for the application of pasty two- or multi-component systems have been known for decades. The following documents are cited for exemplary purposes, CH 669 164 A5, EP 0 607 102 A1, EP 0 236 129 A2, DE 3 440 893 A1, U.S. Pat. No. 4,690,306 A, US 2009/062808 A1, EP 0 787 535 A1, WO 2006/005 206 A1, EP 0 693 437 A1, EP 0 294 672 A, EP 0 261 466 A1, and EP 2 008 707 A1. The pasty two- or multi-component systems are mixed right before their application, usually through the use of static mixers. The following documents are cited for exemplary purposes, GB 1,188,516 A, U.S. Pat. No. 2,125,245 A, U.S. Pat. No. 5,968,018 A, U.S. Pat. No. 4,068,830 A, US 2003/179648 A1, EP 0 664 153 A1, and EP 0 289 882 A1. After the cartridges are filled with reactive pastes, the cartridges need to remain safely closed until their application. In this context, mobile plungers, which are also used to dispense the cartridge content, usually seal the cartridge floors.

A number of solutions have been proposed for closing the cartridge system head of the cartridge system. One simple, but very effective, principle is to close the cartridge head with a closure that can be rotated (EP 0 431 347 A1, DE 2 017 292 A1, U.S. Pat. No. 3,215,298 A). The closure is unscrewed prior to the application. Subsequently, a dispensing tube is screwed into a thread on the cartridge head or fixed through a peg system that simulates a thread. In the interim between the cartridges being opened and the dispensing tube being inserted, ingredients of the pastes may evaporate, especially if the pastes contain volatile substances.

The closure that is in very common use currently in the adhesives and sealant industry is based on the wall material of the cartridge being provided to be very thin at the cartridge head such that said wall can be perforated easily.

The backside of the cartridges is usually closed by mobile plungers that are designed for expelling the pastes during application. In the case of humidity- and air-sensitive pastes, aluminium cartridges may be used that are closed by plastic plungers and over which aluminium cylinders that are closed on one side are pressed in for sealing purposes. During the application of the pastes, the aluminium cylinder having one closed side is moved jointly with the plunger towards the front in the direction of the cartridge head through the action of cartridge applicator guns and the paste is expelled in the process. However, any contact of paste and aluminium surfaces may be problematic in medical applications.

Using cartridge systems for sterile pasty medical products, there is a need for not only the pastes, but obviously the cartridges and secondary packaging means also to be provided in sterile form to the user. For example after aseptic filling of the previously sterilised cartridges, these may be transferred directly to sterile packaging means. Moreover, it may make sense for certain products to sterilise the surfaces of filled cartridges jointly with the packaging means after packaging is completed. Aside from gamma sterilization, which cannot be used with paste systems that can be polymerised, there is the option to use ethylene oxide gas for sterilization.

However, one issue of said sterilization with gas in the case of paste systems containing monomers with a high vapour pressure is that a fraction of the monomers in the cartridges evaporates after the actual sterilization, when the residual ethylene oxide is removed by the action of a vacuum, whereby the monomers form a gas phase in the cartridges and can thus exert a pressure against the plungers. This means that the plungers are moved in the direction of the cartridge floors in undesired manner and may be expelled from the cartridges in the extreme case such that the pastes may leak out.

With regard to the application of bone cements for fixation of total joint endoprostheses, it is always necessary to take into consideration that the OR staff is under time pressure during these surgeries. Therefore, as a matter of principle, cartridge systems for medical applications involving the application of paste-like polymethylmethacrylate bone cements should be designed such that they are largely resistant to user errors and can be operated rapidly and safely even in stressful situations.

The methylmethacrylate monomer is an essential ingredient of paste-like polymethylmethacrylate bone cements. Said monomer evaporates readily and has a relatively high vapour pressure at room temperature. For this reason, it is essential to note with regard to the use of methylmethacrylate-containing pastes that the cartridge plungers in the cartridges may be moved and may be expelled from the cartridges in the extreme case by the evaporating methylmethacrylate upon exposure to a vacuum, such as during the degassing as part of ethylene oxide sterilization.

Polymethylmethacrylate bone cements have been in use in medicine for decades for permanent mechanical fixation of total joint endoprostheses. They are based on powder-liquid systems. Recently, polymethylmethacrylate bone cements that are based on the use of cement pastes have been proposed as well (DE 10 2007 050 762 A1, DE 10 2008 030 312 A1, DE 10 2007 052 116 A1). Cartridge systems comprising at least two cartridges having one feed plunger each are well-suited for this type of starting components of mixing wares. In order to achieve homogeneous mixing of the starting components, it is necessary to shift the feed plungers in parallel. For this purpose, it has been proposed to connect the feed plungers of the two cartridges at their ends protruding from the cartridges.

A generic cartridge system of this type having two cartridges and two feed plungers that are connected to each other is known from U.S. Pat. No. 4,260,077 A. Basically, the cartridge system is structured alike two syringes that are situated right next to each other and whose feed plungers can be connected to each other at the end that is on the side of the cartridge floor. A common outlet opening for both cartridge contents is provided on the tip of the cartridge system. When the contents are squeezed out, the feed plungers are pressed into the cartridges until the front ends of the feed plungers touch against the cartridge heads or until the connection of the feed plungers touches against the cartridge walls on the cartridge floor.

This is disadvantageous in that the feed plungers cannot be propelled through the application of pressure to the cartridge floor, i.e. through a compressed gas. For automatic propulsion of the feed plungers, a mechanical propelling mechanism needs to be provided.

SUMMARY OF THE INVENTION

It is therefore the object of the invention to provide a cartridge system, in which the feed plungers can also be moved through gas pressure.

Said object is met in that the at least two feed plungers are fixedly connected to each other through at least one fin, the cartridge walls of the cartridges that are connected through the fin or fins comprise slits that are arranged parallel to the cartridge axis, whereby the width of the slits is well-suited for taking up the fin or fins, and the at least one fin moves through regions of the slits when the feed plungers perform a motion in the cartridges.

In this context, the invention can provide the slits to extend in length from the region of the cartridge floor to at least half of the length of the cartridge.

The invention can provide just as well for the cartridge walls to be fully slitted by the slits at the cartridge floor.

The invention also proposes a mixing space to be arranged parallel between the cartridges, in particular such that regions of the cartridge walls are provided jointly with the mixing space walls of the mixing space, whereby the mixing space walls are also slitted in the places in which the slits are situated.

In this context, the interior of the mixing space can be provided to have a mobile rod arranged in it parallel to the feed plungers and fixedly connected to the feed plungers through at least one fin, whereby the rod comprises a snap-in locking means on the side facing the outlet opening and an opposite snap-in locking means is attached in the mixing space that acts in concert with the snap-in locking means of the rod in a manner such that a motion of the rod out of the mixing space and therefore a motion of the feed plungers out of the cartridges is significantly hampered, in particular is prevented.

The invention can also provide that the cartridges each comprise at least one opening in the cartridge walls connecting the cartridges to the mixing space, that a closure is arranged in the mixing space or at the cartridge head such that it can be shifted in the mixing space or a closure is suspended at the cartridge head such that it can be rotated, both in appropriate manner such that the closure closes the openings of the cartridges when in a starting position and in that the openings are opened, at least partly, in a final position of the closure, whereby the closure can be shifted or rotated from the starting position to the final position.

In this context, it can be advantageous to have a limit stop, preferably in the form of pegs or fins, be arranged in the mixing space and limiting the motion of the shiftable closure in the mixing space thus define the final position of the shiftable closure.

Moreover, the invention also proposes to arrange the outlet opening in a cartridge system head and the cartridge system head to comprise a fastening means for fastening a dispensing tube, in particular on the inside of the cartridge system head, preferably a thread or multiple pegs.

Another embodiment of the cartridge system according to the invention can provide the feed plungers to close the cartridges in a tight, in particular gas-tight, manner.

Moreover, cartridge systems according to the invention can be characterised in that the fin or at least one of the fins is fixedly connected on the floor-side to the feed plungers, and a locking means is connected to said at least one fin, whereby the locking means extends into a region parallel to or in between the cartridges and engages an opposite locking means therein such that the at least one fin and the feed plungers are prevented from performing a motion in the direction of the cartridge floor.

In this context, the invention can provide in said region an unlocking facility, which is fixedly connected to the shiftable closure such that shifting the closure into its final position is associated with unlocking of the locking means such that the at least one fin and the feed plungers are enabled to perform a motion in the direction of the cartridge floor.

Moreover, the invention proposes that the feed plungers cover the slits on the inside of the cartridges.

And lastly, the invention can provide the feed plungers and the cartridge walls to be built to be gas-tight and flush with each other such that the feed plungers can be pressed into the cartridges through a gas pressure acting on the cartridge floor.

The cartridge system according to the invention is based on the surprising insight that slits in the cartridge walls allow a fin to be used for connecting the feed plungers, whereby the fin is moved into the cartridges through the slits provided in the cartridge walls when the feed plungers are moved. This allows the fin to be arranged to be flat against the feed plungers in the region of the cartridge floor. The fin does not necessarily have to be fastened directly to the cartridge floor or at the ends of the feed plungers facing the cartridge floor, but can just as well be displaced a bit further in the direction of the centre of the cartridge system. Since the feed plungers are pressed into the cartridges, i.e. are lowered into them, i.e. do not project from the cartridges in this arrangement, the feed plungers can be moved by means of compressed air.

A cartridge system of this type can be made altogether of inexpensive injection moulding parts. The cartridge system enables the plungers to be moved synchronously in the cartridges in the direction of the cartridge system head upon application of a force, and thus allows the pastes to be squeezed out evenly in order to ensure the proper mixing ratio of the pastes with respect to each other.

Further simplification and assurance of the operability of a cartridge system according to the invention is provided through the fact that a locking mechanism can safely prevent a motion of the feed plungers upon the action of a vacuum.

In the scope of the invention, the mixing space is understood to be the space situated between the at least two cartridges as well as the adjoining regions. It extends from the cartridge floor, i.e. the rear, floor-side part of the cartridge system, to the outlet opening on the cartridge system head on the front side of the cartridge system, and thus also comprises the internal space of the cartridge system head. In this context, the mixing of the starting components does not have to proceed in every space of the mixing space, but may proceed in sub-regions thereof. A mixing space that is connected to the cartridges through hoses, such that the mixing space is not situated exactly between the cartridges in a geometrical sense, is also included in the scope of the invention.

A shiftable closure in the scope of the present invention is also understood to be a closure which is initially, in the starting position, connected through a fixed connection to the walls of the intervening space, for example through thin bridges, provided said fixed connection includes predetermined breakage sites, which break when a force acts on the closure and thus facilitate the shifting of the closure under the action of a force.

In this context, the invention proposes the fixed connection or fixed connections having the predetermined breakage sites to be provided in the direction, viewed from the openings of the cartridges, in which the closure moves during the opening process in order to prevent particles of the predetermined breakage sites from entering into the mixing ware and/or into the starting components of the mixing ware.

In the scope of the invention, the final position of the closure is not to be understood as a conclusive final position. Accordingly, it would be conceivable, for example, that the shiftable closure can also be moved from the final position into the starting position then rendering the cartridges of the cartridge system ready for re-filling. This renders the cartridge system re-usable. Moreover, the starting position, like the final position, is understood to be just one of at least two positions into which the shiftable closure can be shifted.

In the following, exemplary embodiments of the invention are illustrated through sixteen schematic drawings.

DETAILED DESCRIPTION OF THE INVENTION

Figure 1:
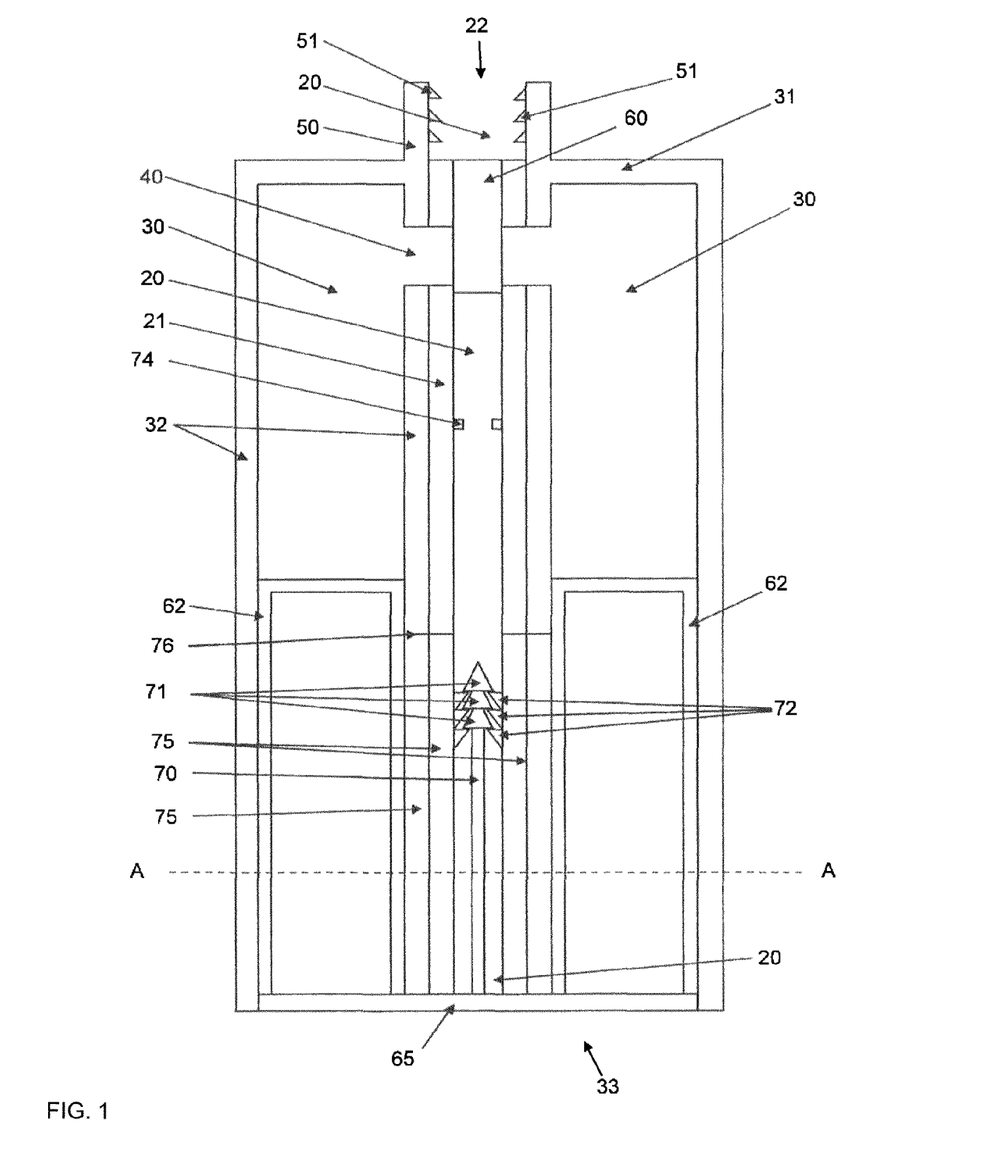
FIG. 1: shows a cross-sectional view in longitudinal direction of a cartridge system according to the invention.

FIG. 1 shows a cross-sectional view of a cartridge system (1) according to the invention having a mixing space (20) that is bounded by mixing space walls (21) and ends into an outlet opening (22). The mixing space (20) extends in the space between two cartridges (30) and is provided as a cylindrical hollow body. The cartridges (30) are bounded by cartridge heads (31), cartridge walls (32), and a cartridge floor (33). The starting components (not shown) for a mixing ware to be mixed are situated inside the cartridges (30). Openings (40) are situated in the cartridge walls (32) and mixing space walls (21) and connect the inside of the cartridges (30) to the inside of the mixing space (20). Accordingly, said cartridge system (1) is suitable for mixing a mixing ware consisting of two components.

The outlet opening (22) is formed in a cartridge system head (50) that comprises, on the inside, a fastening means (51) in the form of a thread or in the form of pegs which may also form a thread.

A shiftable closure (60) in the form of a massive cylinder is placed in press-fit manner in the upper end of the mixing space (20), i.e. the end facing the outlet opening (22). The shiftable closure (60) closes the openings (40) that connect the inside of the cartridges (30) to the inside of the mixing space (20). However, the shiftable closure (60) can just as well possess a closed jacket surface.

Towards the cartridge floors (33), the cartridges (30) are closed through feed plungers (62). The feed plungers (62) that can be shifted in the longitudinal direction of the cartridges (30) can be equipped with customary stripping lips and gaskets at the ends of the feed plungers (62) facing the cartridge head (31) in order to ensure that the cartridges (30) are closed tightly.

The feed plungers (62) are connected to each other on the cartridge floor (33) through a fin (65) or a plate (not shown). An additional fin extending through the mixing space walls (21) and through the cartridge walls (32) can be provided a bit further in the direction of the inside of the cartridge system (1) in order to provide more stability and assured guidance to the arrangement.

In addition, a rod (70) is fixedly connected to the fins (65) and projects into the end of the mixing space (20) facing the cartridge floors (33). Snap-in locking means (71) are provided on the tip of the rod (70). Opposite snap-in locking means (72) engaging the snap-in locking means (71) are attached to the internal walls (21) of the mixing space (20). The opposite snap-in locking means (72) are made of a flexible material, for example rubber. The snap-in locking means (71) can be made of a common plastic material. When the rod (70) is slid into the mixing space (20) deeply enough for the snap-in locking means (71) to engage the opposite snap-in locking means (72), any motion of the rod (70) out of the mixing space (20) is prevented. At the same time, it is feasible without any difficulty to slide the rod (70) deeper into the mixing space (20).

Accordingly, what is situated in the mixing space (20) is the rod (70) that is arranged in longitudinal direction of the feed plungers (62) in a manner such that one end of it is fastened to the fins (65) and that it has a length equal at least to the length of the feed plungers (62). What is essential is that the rod (70) is cogged on the side facing the cartridge head (31). The cogs are oriented such that the tips of the cogs point in the direction of the cartridge floor (33). The rod (70) has a cross-section that is smaller than the cross-section of the mixing space (20).

A flexible snap-in device (72), whose cross-section is smaller than or equal to that of the cogged rod (70), is arranged on the end of the mixing space (20) on the side facing the cartridge floor (33). This means that the cogged rod can snap-in into said snap-in device (72). The snap-in device (72) is arranged in a manner such that the cogged rod (70) can only move in the direction of the cartridge head (31). A retrograde motion towards the cartridge floor (33) is not feasible.

The position of the feed plungers (62) in the cartridges (30) is fixed through the cogged rod (70) and the snap-in device (72) such that a retrograde motion of the feed plungers (62) out of the cartridges (30) is safely prevented even upon the action of a vacuum.

The shiftable closure (60) can be shifted through the outlet opening (22) towards the cartridge floor (33) by the action of a force. The force can be made to act by inserting a suitable dispensing tube (not shown) into the outlet opening (22). A limit stop (74) attached in the form of pegs on the internal walls (21) of the mixing space (20), prevents the shiftable closure (60) from being slid beyond the limit stop (74) into the mixing space (20). In this manner, the limit stop (74) defines the final position of the shiftable closure (60).

In order to allow the fins (65) to move through the mixing space walls (21) and the cartridge walls (32) facing the mixing space (20), these are provided with a slit (75) that extends from the cartridge floors to the slit end (76) on the inside of the cartridge system (1). The fins (65) can move through said slit (75) without any difficulty. This allows the feed plungers (62) to be pressed into the inside of the cartridges (30) upon the application of gas pressure to the cartridge floor (33). The cartridge walls (32) being bordered assures that the gas pressure acting on the floors of the feed plungers (62) is maintained even when these are already situated deep inside the cartridges (30).

The motion of the system consisting of feed plunger (62), rod (70) with snap-in means (71), and fin (65) comes to a standstill only when the fin (65) reaches the slit end (76).

It is important to note that the cartridge system (1) according to the invention can be implemented without difficulty without having the closure (60), the mixing space (20) having the mixing space walls (21), the rod (70) having snap-in means (71), and the cartridge system head (50). Referring to FIG. 1, this means that the region in the middle can also be left out provided the outlet opening (22) is retained. Accordingly, it is fully sufficient to provide two parallel cartridges (30) right next to each other, jointly connected to a common outlet opening (22), which are fixedly connected to a fin (65) in the region of the cartridge floor (33), whereby slits (75) are provided in the cartridge walls (32) for connecting the fin (65).

A gas pressure from the direction of the cartridge floor (33) must also press onto the floor-side regions of the slits (75) and the slits (75) must not be connected to their surroundings in such a manner that a pressure acting on the feed plungers (62) can escape when these are already partly pushed into the cartridges (30). It is best for the slits (75) to be fully separated from the surroundings in a gas- and pressure-tight manner. Likewise, the feed plungers (62) should be separated from the inside of the cartridges (30) in a gas- and pressure-tight manner. Pressure seals of this type (not shown) for moving parts are customary in the trade and are easily available.

Figure 2:
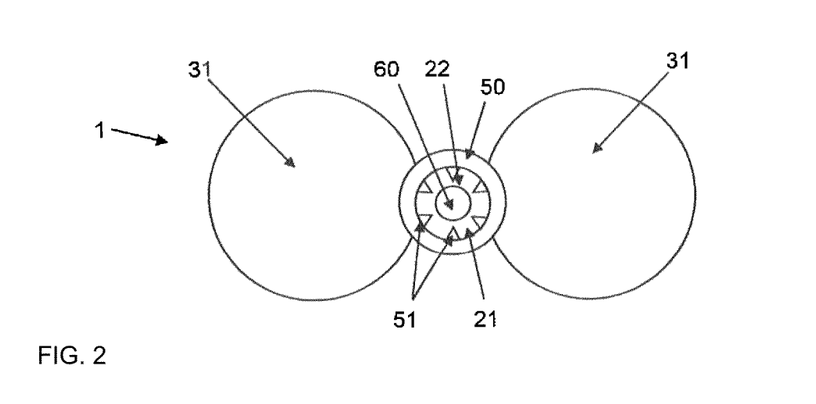
FIG. 2: shows a top view onto the front side of a cartridge system according to the invention having the outlet opening according to FIG. 1.

FIG. 2 shows a top view onto a cartridge system (1) of this type according to FIG. 1, more specifically onto the cartridge system head (50). A glance into the outlet opening (22) shows the mixing space walls (21), the fastening means (51), and the shiftable closure in the middle (60). The cartridge heads (31) of the cartridges (30) situated underneath (not shown in FIG. 2) are provided on both sides of the cartridge system head (50).

Figure 3:
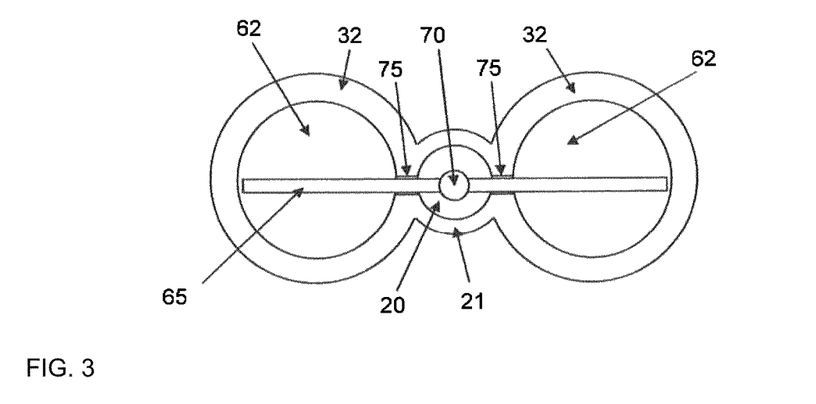
FIG. 3: shows a top view onto the cartridge floor of a cartridge system according to the invention according to FIG. 1.

FIG. 3 shows a top view onto a cartridge system (1) of this type from the direction of the cartridge floor (33). Bounded by the mixing space walls (21), the mixing space (20) is flanked on both sides by the cartridges (30) of which only the cartridge walls (32) and the feed plungers (62) are shown. The rod (70) that projects into the inside of the mixing space (20) is situated in the middle of said mixing space (20) that is open in this direction. The rod (70) and the feed plungers (62) are fixedly connected to each other through the fin (65). In order to allow for motion of the fin (65) into the inside of the cartridge system (1) when the feed plungers (62) move into the cartridges (30), a slit (75) is provided in the walls (21, 32) of the mixing space (20) and of the cartridges (30).

Figure 4:
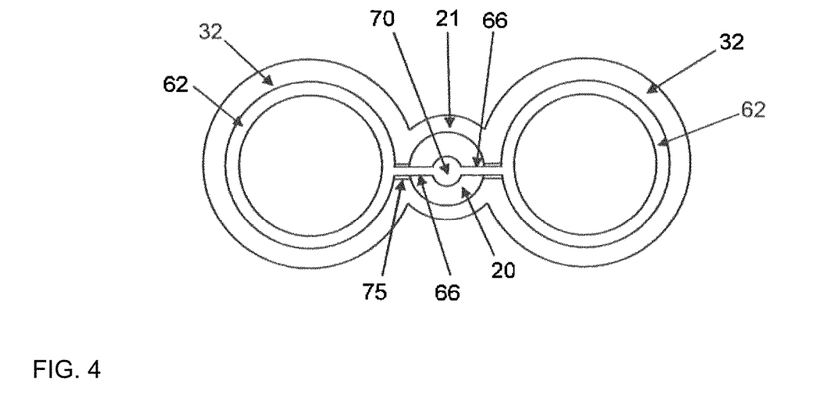
FIG. 4: shows a cross-sectional view of a cartridge system according to FIG. 1 along the section, AA, in FIG. 1.

FIG. 4 shows a cross-sectional view of a cartridge system (1) of this type along the section, (A-A), in FIG. 1. Bounded by the mixing space wall (21), the mixing space (20) is situated between the two cartridges (30) that can be seen through the feed plungers (62) and the cartridge walls (32). The feed plungers (62) are structured to be hollow cylinders that are closed on both sides. The inside of the mixing space (20) has the rod (70) arranged in it. The rod (70) and the feed plungers (62) are connected to each other through the fin (65). Slits (75) are provided in the walls (21, 32) connecting the cartridges (30) to the mixing space (20) and allow the fin (65) connecting the feed plungers (62) in their middle to move on the inside of the cartridge system (1). An additional fin (not shown) can be provided further inside the cartridge system (1) and can also be movable through the slits (75).

Figure 5:
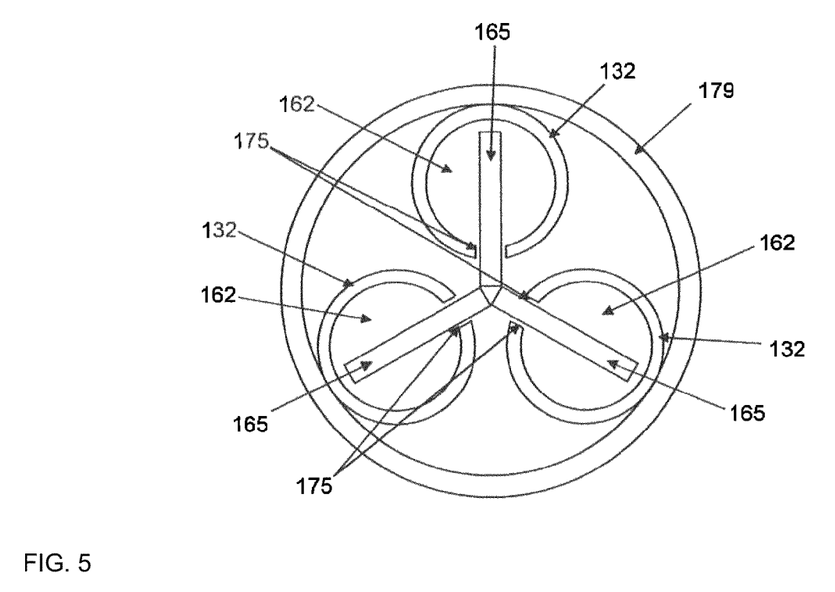
FIG. 5: shows a top view onto a cartridge floor of a second cartridge system according to the invention.

FIG. 5 shows a top view onto a cartridge floor of an alternative cartridge system for mixing a mixing ware consisting of three components. For this purpose, the cartridge system comprises three cartridges of which only the cartridge walls (132) and the feed plungers (162) can be seen from the direction of the cartridge floor. An empty space exists between the cartridge walls (132). A closed mixing space may be arranged in this place just as well. The feed plungers (162) are fixedly connected to each other through fins (165). The entire cartridge system is enclosed through an additional jacketing (179) that positions the cartridges through a connection to the cartridge walls (132).

Slits (175) that are wider than the fins (165) are thick are provided in the cartridge walls (132). It is sufficient if the widths of the slits (175) are equal to the thicknesses of the fins (165). Although this would lead to some friction between the fins (165) and the slit walls, this friction is non-critical provided the force exerted on the feed plungers (162) is larger than the frictional forces. The jacketing (179) can be closed on the cartridge head (not shown) such that a gas pressure can be made to act on the entire cross-section of the jacketing (179). The gas pressure thus exerts a force on the feed plungers (162). Only the ambient pressure acts on the outlet opening (not shown) that is arranged in the region of the cartridge heads and through which all cartridges are connected. The pressure difference between the back, from the direction of the viewer, and the front, in the direction of the outlet opening, makes the feed plungers (162) move.

Figure 6:
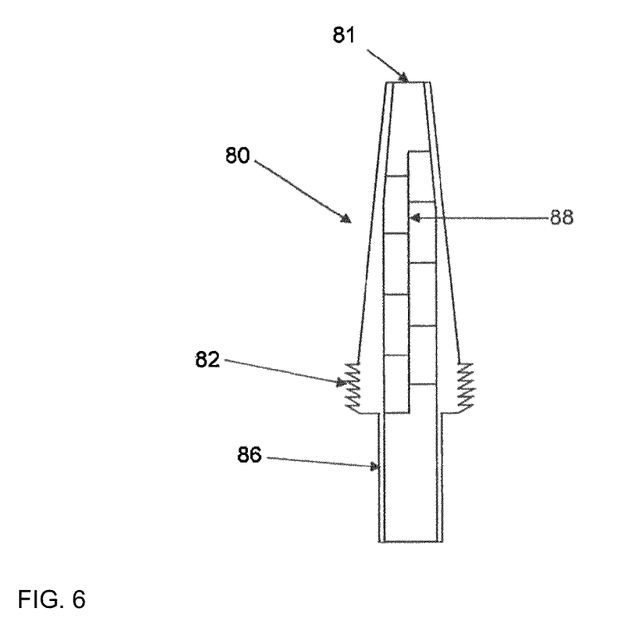
FIG. 6: shows a cross-sectional view in longitudinal direction of a dispensing tube for a cartridge system of this type.

FIG. 6 shows a cross-sectional view of a dispensing tube (80) for a cartridge system (1) according to the invention. The dispensing tube tip (81) that serves for application of a mixed mixing ware is situated on the top end of the dispensing tube (80). Situated underneath, there is an external thread (82) that can be used to screw the dispensing tube (80) into the internal thread (51) of the cartridge system (1). Openings (not shown) can be provided in an extension (86) that is arranged underneath.

The external diameter of the extension (86) is the same as or smaller than the diameter of the mixing space (20). By this means, when the dispensing tube (80) is being screwed into the cartridge system head (50), the extension (86) can penetrate into the mixing space (20) beyond the cartridge system head (50) and thus slide the shiftable closure (60) deeper into the mixing space (20). This opens the openings (40) to the mixing space (20). The extension (86) is provided as hollow cylinder and the openings serve to not block the starting components to be mixed, which pass through the openings (40) in the cartridge walls (32). Accordingly, the materials to be mixed pass through openings (40). A static mixer (88) is provided on the inside of the dispensing tube (80).

However, an extension (86) might also be formed by a rod that ends in a tee piece, which is provided, for example, as an extension of the central axis of the static mixer (88). An extension (86) of this type would then not need to have additional openings. Just as well, an extension of the static mixer (88) beyond the external thread (82) might serve as extension (86).

Figure 7:
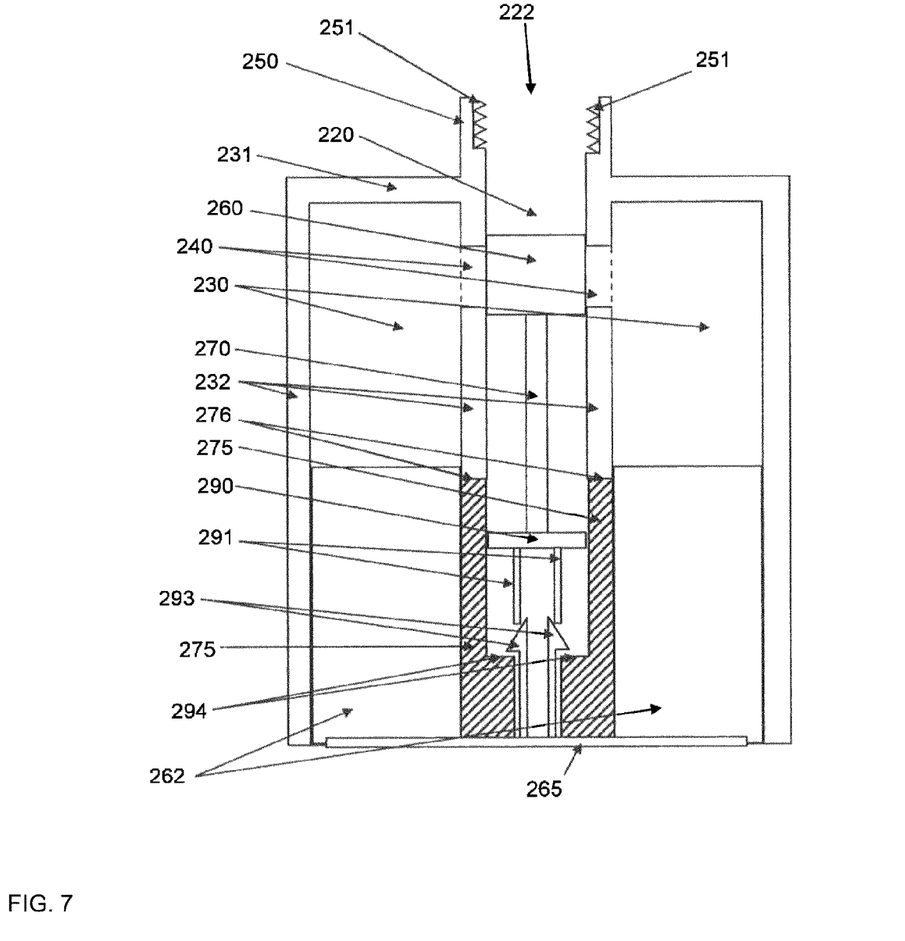
FIG. 7: shows a cross-sectional view of a third cartridge system according to the invention having an unlocking device attached to the closure.

FIG. 7 shows a schematic cross-sectional view of a third exemplary embodiment of a cartridge system according to the invention. This exemplary embodiment has a rod (270) arranged on a closure (260), which rod (270) projects from a centring facility (290) in the centre of a mixing space (220) that is provided as a hollow body. An unlocking facility (291) in the form of a hollow cylinder is arranged on the rod (270) and/or the centring facility (290) thereof. The closure (260) closes openings (240) in the cartridge walls (232), which connect the cartridges (230) to the mixing space (220). A cartridge system head (250) having fastening means (251) for fastening a dispensing tube is situated at the cartridge head (231) on the front end of the cartridge system. The cartridge system head (250) is structured to be a hollow cylinder that forms an outlet opening (222) on the inside.

On the floor side, the cartridges (230) are closed through feed plungers (262). The feed plungers (262) are connected to each other through a fin (265). Slits (275) are provided in the cartridge walls (232) and have a sufficient width to allow a motion of the fin (265) through the slits (275). The region, in which the cartridge walls (232) are slitted, extends to the slit end (276) on the inside of the cartridge system and is shown hatched.

Two locking hooks (293) are connected to the fin (265). Other locking means (293) may be used instead of the locking hooks (293). The locking hooks (293) are made of a flexible material such that they can be squeezed together relatively easily. A locking step (294) is arranged in the region of the locking hooks (293) in the mixing space (220) such that the hooks of the locking hooks (293) can engage the locking steps (294).

In its starting state, the closure (260) closes the openings (240). The locking hooks (293) prevent a motion of the fin (265), and thus of the feed plungers (262) connected to the fin (265), out of the cartridges (230).

If a dispensing tube having an extension, like the one according to FIG. 6, is incorporated into the outlet opening (222), the openings (240) are exposed and the unlocking facility (291) is slid over the locking hooks (293) in a manner such that these are squeezed together and thus a motion of the fin (265) away from the outlet opening (222) and thus a motion of the feed plungers (262) out of the cartridges (230) is made feasible.

Accordingly, the hollow cylinder (291) arranged on the centring facility (290) is slid over the locking hooks (293) concurrently with the insertion of the dispensing tube, whereby the locking hooks (293) bend perpendicular to the longitudinal axis of the mixing space (220), and whereby the locking pegs of the locking hooks (293) move away from the locking step (294) and thus the locking of the fin (265) is being unlocked.

One variant of the invention is characterised in that an internal thread (251) or snap-in closure is arranged on the side of the mixing space (220) facing the cartridge system head (250), in that a closure (260), which can be shifted in longitudinal direction of the cartridges (230), is situated in the mixing space (220) in a press-fit manner and is closed on the side facing the cartridge system head (250) over its surface perpendicular to the longitudinal axis of the hollow space (220), in that the shiftable closure (260) is arranged over the openings (240) of the cartridges (230), in that the shiftable closure (260) is connected through a rod (270) to a circular or star-shaped centring disc (290) on the underside of which a hollow cylinder (291) is arranged, in that the hollow cylinder (291) has a diameter that is smaller than the internal diameter of the mixing space (220), in that an external thread or a hollow cylinder having pegs for a snap-in mechanism is arranged on one end of an insertable dispensing tube, and in that an extension that has perforations at its cylinder jacket, i.e. is provided with openings, and is provided in the form of a hollow cylinder or any other perforated hollow body that is open in longitudinal direction and has a perforated jacket surface, is arranged in longitudinal direction on the end of the external thread or of the cylinder having pegs.

The advantage of this arrangement is that the cartridges (230) are being opened and the dispensing tube is being inserted concurrently, and the cartridge floors that are closed by the fin (265) with the feed plungers (262) are released concurrently as well. Accordingly, the user can insert the starting components-filled cartridge inserts in the respective cartridge applicator gun/cement gun used to operate the cartridge system only, if, firstly, the dispensing tube is inserted and, secondly, the fin (265) with the feed plungers (262) used to close the cartridge floors is unlocked and removed. Accordingly, it is impossible to insert cartridge inserts in cartridge applicator gun or cement guns for operation of the cartridge system unless the dispensing tube is inserted and unless the cartridges (230) are open. This renders faulty operation virtually impossible.

In the same way, in which the fin (265) can be moved through the slit (275), the fin also moves through the locking hooks (293), unlocking facility (291), centring facility (290), and rod (270) and/or past them. Likewise, the locking hooks (293) might jointly move with the fin (265) through these parts and/or past these parts after deformation of the locking hooks (293) through the unlocking facility (291). The invention can just as well provide the locking hooks (293) to be broken off during the unlocking.

Figure 8:
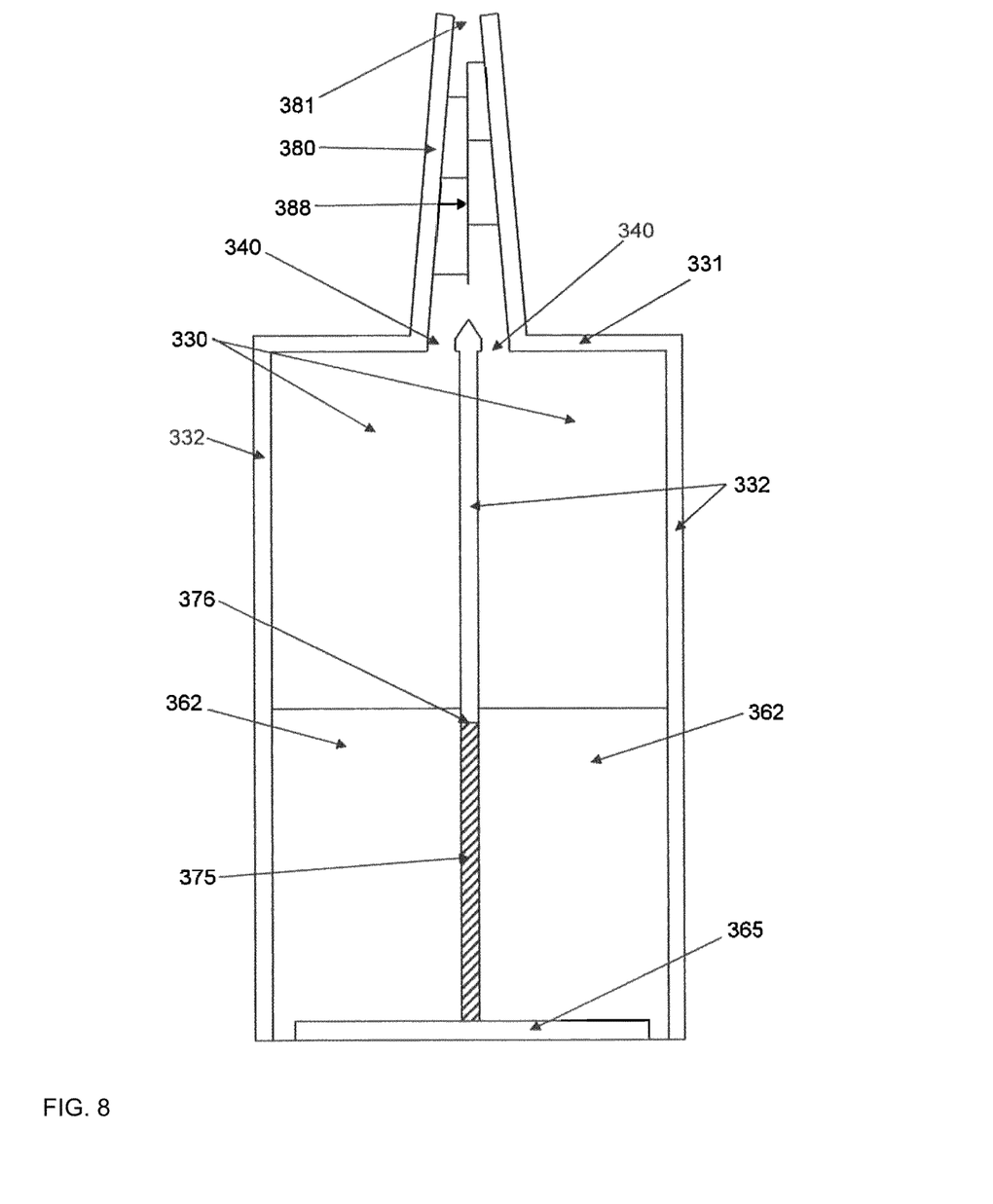
FIG. 8: shows a fourth cartridge system according to the invention having a dispensing tube.

FIG. 8 shows in another schematic drawing the cross-section of a fourth exemplary embodiment that has a simple design. The internal spaces of two immediately adjacent cartridges (330) are connected to each other through openings (340) in the cartridge heads (331). On the floor side, the cartridges (330) are closed through feed plungers (362) in a gas-tight manner. A dispensing tube (380) ending in a dispensing tube tip (381) is arranged on the cartridge head (331) over the openings (340). A static mixer (388) is provided on the inside of the dispensing tube (380) and is meant to attain more extensive mixing of the mixing ware to be generated. However, the static mixer (388) can just as well be left out and is not essential for the present invention.

The two feed plungers (362) are connected to each other through a fin (365). The fin (365) can, for example, have a rectangular profile. In the starting state of the cartridge system, the feed plungers (362) are flush with the cartridge wall (332). In order to enable the feed plungers (362) to move further into the inside of the cartridges (330), the cartridge walls (332) through which the two cartridges (330)

are connected to each other, are provided with a slit (375). The slitted region (375) of the cartridge walls (332) is shown hatched.

In the starting state of the cartridge system, the fin (365) is situated in the slit (375) at its cartridge floor-side end. The slit end (376) is situated in the region of the centre of the cartridge system. The feed plungers (362) extend more deeply into the cartridges (330) than the slit (375). When a gas pressure is exerted on the fin (365) and the feed plungers (362), the feed plungers (362) are driven more deeply into the cartridges (330). The fin (365) moves through the slit (375) concurrently. The motion ceases when the fin (365) arrives at the slit end (376) or when the feed plungers (362) arrive at the cartridge head (331).

The end of the feed plungers (362) facing the cartridge head (331) have a sealing means sealing the internal space of the cartridges (330) above the slit end (376) in a gas- and pressure-tight manner arranged on them.

All embodiments described can be applied without any difficulty to cartridge systems having three, four or even more cartridges for the mixing of a mixing ware made of three, four or even more components. With regard to the use with very many components, it is expedient not to provide the cartridges to be cylindrical in shape, but rather in the form of segments.

The term, cartridge system, is understood to refer to cartridges that are made up of two, three, four, five or more cartridges (30, 230, 330), whereby the individual cartridges (30, 230, 330) are arranged to be parallel to each other. The cartridges (30, 230, 330) can be structured to be cylinder-shaped or be hollow bodies having a different axial symmetry. These are so-called side-by-side cartridges. The cartridges can already be filled with starting components for a mixing ware to be mixed, but can just as well be empty, i.e. may still need to be filled with content, e.g., cartridge inserts.

The shiftable closure (60, 260) preferably has a closed jacket surface. It is essential that the cartridges (30, 230, 330) are closed through feed plungers (62, 162, 262, 362), whereby the feed plungers (62, 162, 262, 362) are connected to each other through fins (65, 165, 265, 365) on the side facing away from the cartridge floor (33). This means that the feed plungers (62, 162, 262, 362) form a unit and cannot be moved individually. This enables the pastes of the cartridge system to be expelled evenly from all cartridges (30, 230, 330). This feature is essential if the plungers are to be moved by direct application of compressed gas.

Another advantage of an embodiment of the cartridge system according to the invention is that all openings (40, 240) in the cartridges (30, 230) are closed through only one shiftable closure (60, 260). Said closure has a slightly larger cross-section than the mixing space (20, 220). This means that the jacket surface of the shiftable closure (60, 260) is being pressed against the internal wall of the mixing space (20, 220) and/or the walls (21) thereof. When the shiftable closure (60, 260) is situated over the openings (40, 240, 340) of the cartridges (30, 230), the same are closed. In this context, the shiftable closure (60, 260) completely overlaps the openings (40, 240, 340) in a manner such that sufficient closed jacket surface to provide for sealing touches against the internal wall (21) of the mixing space (20, 220). Sealing is attained through the contact pressure resulting from the tight contact of the jacket surface of the shiftable closure (60, 260) to the internal wall (21) of the mixing space (20, 220).

Many common plastic materials in medicine, such as polypropylene, have only low coefficients of static friction and dynamic friction. This means that sliding processes can be made to proceed by the action of relatively small force in the case of tribological pairs made of such plastic materials. The shiftable closure (60, 260) can therefore be shifted through axial motion if suitable plastic materials are used. Through this means, it is feasible to move the shiftable closure away from the openings (40, 240, 340) of the cartridges (30, 230, 330) and thus open the cartridges (30, 230, 330). Therefore, when the shiftable closure (60, 260) moves axially, the openings (40, 240, 340) of all cartridges (30, 230, 330) can be opened synchronously.

When the dispensing tube (80) is being screwed in, the extension (86) moves along in the direction of the cartridge floor (33). This causes a force to be applied to the shiftable closure (60, 260) in the direction of the cartridge floor (33). As soon as the static friction between the jacket surface of the shiftable closure (60, 260) and the internal wall (21) of the mixing space (20, 220) is overcome, the shiftable closure (60, 260) can move in the direction of the cartridge floor (33). In the course of this forced motion of the shiftable closure (60, 260), which is caused by the dispensing tube (80) being fastened, the openings (40, 240) of the cartridges (30, 230) are opened synchronously. Here, the perforations and/or openings (not shown) of the extension (86) are situated over the openings (40, 240) of the cartridges (30, 230, 330). Through this means, the internal spaces of the cartridges (30, 230, 330) are connected to the internal space of the extension (86), which is provided as perforated hollow cylinder or perforated irregularly- or regularly-shaped hollow body. Moving the feed plungers (62, 162, 262, 362) in the direction of the cartridge system head (50, 250), pastes that are present in the cartridges (30, 230, 330) can enter into the internal space of the extension (86) through the exposed openings (40, 240, 340) and move through the static mixer (88) in the direction of the outlet opening (81) of the dispensing tube (80).

According to the invention, the shiftable closure (60, 260) is preferably provided as hollow cylinder, whereby it is particularly preferred for the hollow cylinder to be closed over the entire cross-section only on the side facing the cartridge head (31, 231, 331). The termination of the closure (60, 260) thus formed, which may, for example, be a disc, prevents the pastes from spreading in the mixing space (20, 220) in the direction of the cartridge floor (33) when the pastes are being expelled.

Being provided as a hollow cylinder with one closed side and an open side in the direction of the cartridge floor (33), the rod (70) can travel a maximal path during the motion of the feed plungers (62) in the direction of the cartridge head (31) in the first exemplary embodiment. For this purpose, the diameter of the tip of the rod (70) including the snap-in locking means (71) attached thereto is smaller than the internal diameter of the shiftable closure (60) that is provided as a hollow cylinder.

It is feasible just as well to provide the shiftable closure (60, 260) as a hollow body having an oval cross-section or a regular or irregular polygonal cross-section. It is feasible just as well to provide the shiftable closure (60, 260) as a solid body or as a body that can be assembled from multiple individual parts. The shiftable closure (60, 260) can be manufactured from one or more material(s), depending on the requirements with regard to the chemical stability to the pastes and the desired sliding properties.

According to the invention, pegs, fins or a ring can be arranged as retaining means (74) on the internal wall (21) of the mixing space (20, 220). They limit the maximal axial shift of the shiftable closure (60, 260) in the direction of the cartridge floor (33) or in the direction of the outlet (22).

According to the invention, the perforated hollow body (86) serving as extension has a length in longitudinal direction of the cartridges (30, 230) that is larger than or at least equal to the length of the openings (40, 240) of the cartridges (30, 230). This ensures that the entire openings (40, 240) of the cartridges (30, 230) can be exposed when the dispensing tube (80) is being fastened. Thus, the entire cross-section of the openings (40, 240) can be exposed.

Moreover, according to the invention, the distance of the holding means (74) in the longitudinal direction of the cartridges (30, 230) to the openings (40, 240) of the cartridges (30, 230) is at least equal to the length of the extension (86) and/or of the closure (60, 260). The retention means (74) are required to ensure that the shiftable closure (60, 260) cannot be moved beyond what was required previously, when the cartridges (30, 230) were opened, upon the pastes being expelled. This means that the retention means (74, 274) also serve to prevent the formation of a dead volume that cannot be utilized.

The cartridges (30, 230, 330) comprise one or more slits (75, 175, 275, 375) from the cartridge floor (33) to at least half of the length of the cartridge, which slits are oriented such as to be parallel to the cartridge axis. If applicable, the mixing space walls (21) also comprise slits (75, 175, 275, 375) that are oriented in the longitudinal direction of the cartridges (30, 230, 330) and are of the same length as the slits (75, 175, 275, 375) of the cartridges (30, 230, 330), whereby the number of slits (75, 175, 275, 375) in the mixing space walls (21) is equal to the number of slits (75, 175, 275, 375) in the cartridges (30, 230, 330), and the slits (75, 175, 275, 375) of the mixing space walls (21) are situated over the slits (75, 175, 275, 375) of the cartridges (30, 230, 330) in such manner that the internal spaces of the cartridges (30, 230, 330) and the mixing space (20, 220) are connected to each other.

According to the invention, the fins (65, 165, 265, 365) have a cross-section that is smaller than the slits (75, 175, 275, 375). This means that the fins (65, 165, 265, 365) can be moved through the slits (75, 175, 275, 375) in the cartridges (30, 230, 330) in the direction of the cartridge system head (50, 250) when the cartridges (30, 230, 330) are being squeezed out. The slits (75, 175, 275, 375) serve as guidance for the fins (65, 165, 265, 365) and thus for the feed plungers (62, 162, 262, 362) during the squeeze-out motion in the direction of the cartridge head (31, 231, 331).

The cartridge system according to the invention is used for packing, storing, and applying paste-shaped bone cements, dental multi-component preparations, adhesives, sealants, cosmetics, and food items. The multi-component cartridge system is particularly well-suited for storing and applying paste-shaped polymethylmethacrylate bone cements.

The features of the invention disclosed in the preceding description and in the claims, figures, and exemplary embodiments, can be essential for the implementation of the various embodiments of the invention both alone and in any combination.

We claim:

1. A cartridge system for mixing and applying a mix, comprising:
   at least two cartridges arranged parallel to each other, having a common outlet opening, a common cartridge floor, an opposite cartridge head and cartridge walls extending between the common cartridge floor and the cartridge head,
   the at least two cartridges laterally positioned side-by-side relative to one another, wherein each of the cartridges is defined by a border of the cartridge walls,
   each of the cartridges comprises a feed plunger for expelling starting components of the mix from the cartridges,
   each feed plunger is fixedly connected to the other feed plunger by a fin,
   each of the cartridges has a slit defined in one of the cartridge walls, wherein each slit is arranged parallel to a longitudinal cartridge axis of a cartridge, a width of each of the slits is matched to accommodate the fin, and the fin moves along the slits when the feed plungers move within the cartridges,
   mixing space walls arranged parallel to the longitudinal cartridge axes of the cartridges and disposed between the cartridges, the mixing space walls define a mixing space between the cartridges, the mixing space accommodates a mobile rod arranged parallel to the feed plungers,
   a complementary snap-in locking mechanism comprising a first part and a second part, wherein the first part of the complementary snap-in locking mechanism is mounted to the mobile rod opposite the common outlet opening and the second part of the complementary snap-in locking mechanism is attached to an interior surface of the mixing space walls, when the first and second parts of the complementary snap-in locking mechanism are engaged in a locked state the fin and the feed plungers are prevented from motion in a direction towards the common cartridge floor.

2. The cartridge system according to claim 1, wherein each of the slits starts at the common cartridge floor and terminates at a slit end disposed at at least half of a distance from the common cartridge floor to the cartridge head.

3. The cartridge system according to claim 2, wherein the feed plungers and the cartridge walls are built to be gas-tight and flush with each other such that the feed plungers are pressed into the cartridges through a gas pressure acting on the common cartridge floor.

4. The cartridge system according to claim 1, wherein each of the slits starts at the common cartridge floor and terminates at the cartridge head.

5. The cartridge system according to claim 1, wherein parts of the cartridge walls are in direct physical contact with the mixing space walls, the mixing space walls having slits at locations corresponding to slits in the cartridge walls.

6. The cartridge system according to claim 5, wherein the mobile rod and the feed plungers are fixedly connected to each other by the fin,
   when the first and second parts of the complementary snap-in locking mechanism are engaged in the locked state motion of the mobile rod out of the mixing space and therefore motion of the feed plungers out of the cartridges is minimized or prevented.

7. The cartridge system according to claim 5, wherein the cartridges each comprise:
   an opening defined in one of the cartridge walls and connecting the cartridges to the mixing space,
   a closure is arranged so as to be translatably moved in the mixing space or rotatably suspended at the cartridge head, such that the closure closes the openings of the cartridges when in a starting position, and in that the openings are at least partly opened, in a final position of the closure, wherein the closure is translatable or rotatable from the starting position to the final position.

8. The cartridge system according to claim 7, further comprising a limit stop mounted to the mixing space walls, limiting the translatable movement of the closure in the mixing space, wherein the final position of the closure is defined by the limit stop.

9. The cartridge system according to claim 8, wherein when the translatably moved closure in the mixing space contacts the limit stop defines a final position of the translatably moved closure.

10. The cartridge system according to claim 8, wherein the limit stop comprises pegs or fins.

11. The cartridge system according to claim 1, wherein the common outlet opening is arranged in a cartridge system head and the cartridge system head comprises a fastener for fastening a dispensing tube.

12. The cartridge system according to claim 11, wherein the dispensing tube is received within the common outlet opening of the cartridge system head.

13. The cartridge system according to claim 1, wherein the feed plungers close the cartridges in a tight manner.

14. The cartridge system according to claim 1, wherein a closure is translatably movable in the mixing space, the cartridge system further comprising an unlocking component provided in the mixing space, the unlocking component is fixedly connected to the closure such that translatably moving the closure into a final position is associated with an unlocked state of the complementary snap-in locking mechanism such that the fin and the feed plungers are movable in a direction towards the common cartridge floor.

15. The cartridge system according to claim 1, wherein the cartridge system mixes and applies a medical cement.

16. The cartridge system according to claim 1, wherein the feed plungers close the cartridges in a gas-tight manner.

* * * * *